United States Patent
Dürr et al.

[11] Patent Number: 6,139,864
[45] Date of Patent: Oct. 31, 2000

[54] COMPOSITIONS FOR COMMON COLDS

[75] Inventors: Tillmann Dürr, Hohen-Sulzen; Bodo Fritzsching, Weinheim; Michael Klingeberg, Worms; Jörg Kowalczyk, Bockenheim; Gunhild Kozianowski, Grunstadt; Markwart Kunz, Worms; Knut M. Rapp, Offstein; Peter J. Sträter, Heidelberg, all of Germany

[73] Assignee: Sudzucker Aktiengesellschaft, Mannheim/Ochsenfurt, Germany

[21] Appl. No.: 09/175,831

[22] Filed: Oct. 20, 1998

[30] Foreign Application Priority Data

Apr. 28, 1998 [DE] Germany .................... 198 18 842

[51] Int. Cl.[7] ................................. A61K 47/00
[52] U.S. Cl. ................ 424/439; 424/440; 424/441; 424/421; 424/410; 424/405; 424/643; 426/322; 426/335; 426/532; 514/25; 514/494

[58] Field of Search ............... 514/25, 27, 32, 514/42, 53, 494; 424/405, 410, 421, 439–441, 643; 426/322, 335, 532

[56] References Cited

U.S. PATENT DOCUMENTS 5,002,970  3/1991  Eby, III ..................... 514/494

FOREIGN PATENT DOCUMENTS

0625578B1  12/1993  European Pat. Off. .
19532396C2  8/1997  Germany .

Primary Examiner—Neil S. Levy
Attorney, Agent, or Firm—Ostrolenk, Faber, Gerb & Soffen, LLP

[57] ABSTRACT

Sugar alcohol mixtures are used as antimicrobially active compounds.

20 Claims, 3 Drawing Sheets

COMPOSITIONS FOR COMMON COLDS

BACKGROUND OF THE INVENTION

The present invention relates to the use of a sugar alcohol mixture containing 6-O-α-D-glucopyranosyl-D-sorbitol (1,6-GPS) and 1-O-α-D-glucopyranosyl-D-mannitol (1,1-GPM) in pharmaceuticals, food products and luxury food products as antibacterially active compounds, in particular in combination with zinc, and to the products containing these substances.

The common cold is a widespread illness which causes unpleasant symptoms. Microorganisms which cause common cold, for example bacteria such as Staphylococcus aureus, or viruses such as rhinovirus, are mainly present in the throat, pharynx and the nasal passages of the organisms which are infected, where it is generally possible to control them directly with active compounds. Suitable administration forms for pharmacologically active compounds are, for example, lozenges or compacts. Such administration forms are characterized in that they are solid formulations which slowly dissolve in the throat and the pharynx and which thereby inhibit multiplication and propagation of the microorganisms which are present on the surface of or on the mucous membranes.

Zinc is known as a pharmaceutically active substance for controlling microorganisms which cause common colds. In a study involving rhinoviruses, it was shown that the antiviral effects are a direct function of the amount of free $Zn^{2+}$ ions (Merluzzi et al., in: Research Communications in Chemical Pathology and Pharmacology Vol. 66, (1989) 3, 425–440). Free, i.e. uncomplexed, zinc ions are nowadays rated as a pharmacological agent which markedly reduces both the duration and the severity of the symptoms of colds (Mossad et al., in: Annals of Internal Medicine, Vol. 125 (1996) 2, 81–87 and Godfrey et al., in: Alternative Therapies, Vol. 2, (1996) 6, 63–72). An essential precondition for the observed therapeutic effect of zinc is the necessity that the pharmaceutic excipient which contains the zinc ions, for example a lozenge, has to be taken and allowed to dissolve in the mouth if possible without interruption once the symptoms have manifested themselves, for example every 1.5 to 2 hours. The reason for this is the fact that the zinc ions act topically in the mouth, the nasal passages and the pharynx.

However, this way of continuously administering active compounds in the mouth has a number of considerable disadvantages, since the mono- and disaccharides which are present in most cases in the pharmaceutical excipient promote caries formation. For this reason, it is advantageous to employ tooth-friendly sugar substitutes as a replacement for the caries-promoting sugar. Sorbitol and mannitol are known to be suitable as sugar substitutes for use in zinc-containing preparations. The use of sorbitol and mannitol, however, has the disadvantage that these compounds dissolve more rapidly in the mouth and the pharynx, so that the relatively long and continuous action time of the zinc ions which is required is not always ensured. Additionally, it is known, for example, from U.S. Pat. Nos. 5,409,905 and 5,002,970 that both sorbitol and mannitol have metal-complexing properties and also complex zinc. From Godfrey et al. in: The Journal of International Medical Research 20 (1992), 234–246 and Zarembo et al., in: Journal of Pharmaceutical Sciences, Vol. 81, (1992) 2, 128–130, it is also known that mannitol and sorbitol have zinc-complexing action, and it is additionally known that mannitol-, sorbitol- and zinc-salt-containing lozenges consequently have a considerably reduced activity with respect to shortening the duration of and lessening the symptoms of colds (Smith et al., in: Antimicrobial Agents and Chemotherapy 33 (1989) 5, 646–648). The mannitol-zinc and sorbitol-zinc complexes which are formed convert the zinc into a pharmaceutically ineffective form.

SUMMARY OF THE INVENTION

The technical object on which the present invention is based thus consisted in providing a product for alleviating and controlling colds, but which simultaneously is acariogenic, has a reduced calorific value and also ensures a continuously efficient release of active compound.

This object is achieved by the present invention by providing the use of a 1,6-GPS- and 1,1-GPM-containing sugar alcohol mixture as antimicrobially active compound in pharmaceuticals, food products and luxury food products. Surprisingly, it has been shown that a mixture of 1,6-GPS and 1,1-GPM, in particular an approximately equimolar mixture of these two sugar alcohols, which is also referred to as isomalt, hydrogenated isomaltulose or Palatinite®, has antimicrobial action and is additionally acariogenic and dissolves more slowly than sorbitol, thus making possible a prolonged release of active compound.

In a particularly advantageous embodiment of the present invention, the 1,6-GPS- and 1,1-GPM-containing sugar alcohol mixture also contains 1,1-GPS (1-O-α-D-glucopyranosyl-D-sorbitol) and, if appropriate, small amounts of hydrogenated or non-hydrogenated mono-, di- and oligosaccharides, xylitol, erythritol, maltitol, hydrogenated glucose syrups and starch syrups, lactitol and also polydextrose. Sugar alcohol mixtures which can be used according to the invention are, for example, known from EP 0 625 578 B1, which is expressly incorporated into the disclosure content of this invention with respect to such sugar alcohol mixtures and their preparation.

In the context of the present invention, a pharmaceutical is an agent which mainly promotes or reestablishes the health of a human or animal body and which may be both of prophylactic and therapeutic nature.

In the context of the present invention, a food product is a product which mainly serves to feed the human or animal body, such as, for example, yogurt, marmalade, preserves, including so-called "functional foods", while a luxury food product is a product which mainly serves for giving a pleasant taste, such as, for example, a chewing gum, a sweet, a candy, a chocolate, a cake, a cookie, a gummy bear or the like.

As mentioned, the mixture used according to the invention of the sugar alcohols, in particular together with zinc, acts as an antimicrobially active compound or active compound mixture, i.e. the mixture has the properties defined below of an antimicrobially active compound. In the context of the present invention, an antimicrobially active compound is an active compound which acts on bacteria, i.e. both Gram-positive and Gram-negative bacteria, protozoa, viruses, bacteriophages, retroviruses, viroids, yeasts, algae, fungi and/or similar microorganisms, the action consisting in an inhibition of growth and/or multiplication and/or in killing the microorganisms, i.e. being microbistatic and/or microbicidal. In a particularly preferred embodiment of the invention, an antimicrobially active compound has, in particular, bacteriostatic and/or bactericidal and/or antiviral activity.

In a particularly preferred embodiment of the present invention, the 1,6-GPS- and 1,1-GPM-containing sugar alcohol mixtures which are used according to the invention are combined with zinc, in particular inorganic or organic zinc salts, such as zinc gluconate or zinc acetate. Surprisingly, it has been found that, in spite of the fact that (as known from the literature) sorbitol or mannitol complex zinc and that therefore sorbitol- or mannitol-containing products having a content of zinc have little if any cold-controlling action, the dissolved 1,6-GPS- and 1,1-GPM-containing sugar alcohol mixtures which are to be used according to the invention which additionally contain zinc display a complexation behavior similar to that which is observed with products based on sucrose/glucose mixtures and that the zinc ions are thus predominantly present in the uncomplexed form and can therefore exert their antimicrobial action. This finding is to be considered surprising, inter alia, because the disaccharide alcohols 1,6-GPS and 1,1-GPM are sorbitol and mannitol derivatives, respectively, which according to expectation should complex zinc to a greater extent. The invention therefore also relates to the use of a mixture of the above-mentioned sugar alcohols and zinc ions as an antimicrobially active compound or as an antimicrobially active compound combination.

In the context of the present invention, free or uncomplexed zinc ions are those zinc ions which in aqueous solution form only the labile aquocomplexes which any ion in aqueous medium has in the form of a salvation sphere. Free or uncomplexed zinc ions are therefore not associated with other substances in the form of a complex.

In a preferred embodiment of the present invention, the proportion of zinc in the sugar alcohol mixture is 0.5–10 mg of zinc per 9 of sugar alcohol, preferably 1–5 mg of zinc per g of sugar alcohol.

The present invention therefore also relates to products, in particular pharmaceuticals, food products and luxury food products, which contain the above-mentioned sugar alcohol mixtures, in particular 1,1-GPM- and 1,6-GPS-containing sugar alcohol mixtures in combination with zinc, in particular with organic or inorganic zinc salts. The ratio of the two sugar alcohols can vary from 1:99 to 99:1 weight parts. In a particularly preferred embodiment of the invention, the ratio by weight of the sugar alcohols 1,1-GPM and 1,6-GPS present in the product 43–57% 1,1-GPM and 57–43% 1,6-GPS, that is, about 1:1, for example, the sugar alcohol mixture of 1,1-GPM and 1,6-GPS which is contained in the product is isomalt. However, according to the invention, it is also possible that the sugar alcohol mixture consists of 1,1-GPM, 1,6-GPS and 1,1-GPS, or contains a mixture of these sugar alcohol mixtures, if appropriate together with residual amounts of other sugar alcohols and oligosaccharides. For instance, one can use 10–50% 1,6-GPS, 2–20% 1,1-GPS and 30–70% 1,1-GPM or one can use 5–10% 1,6-GPS, 30–40% 1,1-GPS and 45–60% 1,1-GPM The products according to the invention may be present in the form of pastilles, tablets, compacts, sprays, mixtures for inhalation, juices, sugar-coated tablets, hard or soft candies, suspensions or the like.

The use according to the invention or the products according to the invention thus have a particularly tooth-friendly matrix in the form of the sugar alcohol mixture to be used according to the invention of 1,1-GPM and 1,6-GPS, if appropriate in combination with 1,1-GPS, where the activity of the zinc ions which may be present against cold-causing microorganisms such as rhinoviruses is not reduced by complexation. The products according to the invention or their use according to the invention are furthermore distinguished by their low dissolution rate in comparison to known products, so that the active compound is released and allowed to act for a long period of time at the desired site of action. Finally, the sugar alcohol mixtures to be used according to the invention are calorie reduced, suitable for diabetics, and they permit the preparation of products having a good storage stability, thus making it possible to use a less expensive packaging.

In a further embodiment, the invention also relates to the above-mentioned uses and to the above-mentioned zinc-containing products, where the sugar alcohol mixture is either a 1,6-GPS-enriched or a 1,1-GPM-enriched mixture, as described in DE 195 32 396 C2. Such enriched mixture generally contains 57–99% of one sugar alcohol and 1–43% of the other. By varying the ratios of the sugar alcohols used, which is made possible according to the invention, it is possible to set desired dissolution rates of the products prepared. Depending on the desired use and the active compound to be administered, a certain ratio of the sugar alcohol mixtures can be set, so that almost any dissolution rates and thus release rates of the pharmacologically active components, in particular zinc, can be set. This is based on the fact that the dissolution kinetics of the sugar alcohols 1,6-GPS, 1,1-GPM and 1,1-GPS differ considerably. Thus, 1,1-GPM has a considerably lower dissolution rate than 1,6-GPS or other substances which are suitable for this application. In cases in which a rapid release of the active compound, in particular of zinc, is desired, mixtures which are enriched in 1,6-GPS according to the invention and have an increased dissolution rate are employed, whereas in cases where a sustained release of the pharmaceuticals is important, use is primarily made of 1,1-GPM-enriched mixtures.

In a particularly preferred embodiment of the invention, the products according to the invention or the sugar alcohol mixture of 1,1-GPM and 1,6-GPS used according to the invention additionally contains intensive sweeteners such as acesulfam-K, aspartam, cyclamate, glycyrrhizine, neotame, neohesperidine DHC, stevioside, sucralose, thaumatine, saccharin or the like. In an advantageous manner, the products according to the invention or the sugar alcohol mixture of 1,1-GPM and 1,6-GPS used according to the invention additionally contain flavorings or aroma ingredients, such as lemon or peppermint aroma. The products according to the invention or the sugar alcohol mixture of 1,1-GPM and 1,6-GPS used according to the invention may also contain food-compatible acids, such as ascorbic acid, malic acid or gluconic acid, and also, as lubricants, fatty acids or salts thereof, such as magnesium stearate or sodium stearate. Finally, the products according to the invention or the sugar alcohol mixture of 1,1-GPM and 1,6-GPS used according to the invention may contain colorants and/or disintegrants, such as modified starch, polyvinylpyrrolidones (PVP) or carboxymethylcellulose.

According to the invention, the products or uses may include, in a preferred embodiment and in addition to the sugar alcohols 1,1-GPM and 1,6-GPS provided by the invention, also enzymes, coenzymes, minerals, vitamins, antibiotics, nicotine, coffee, eucalyptus, codeine, phenacetine, paracetamol, acetylaminophenols, acetylsalicylic acid, menthol or other pharmacologically active compounds (cf. Smit M. B. H. and Feldmann W. "Over-the-counter cold medications: A critical review of clinical trials between 1950 and 1991", in: JAMA 269, (1993) 2258–2263). The pharmaceutically active compounds, in particular zinc, are present in such an amount that they have the desired pharmacological effect.

Further advantageous embodiments of the invention result from the subclaims.

BRIEF DESCRIPTION OF THE DRAWINGS

Other features and advantages of the present invention will become apparent from the following description of the invention which refers to the accompanying drawings.

DETAILED DESCRIPTION OF THE INVENTION

EXAMPLES

Example 1

Antibacterial Effect of Isomalt

Figure 1:
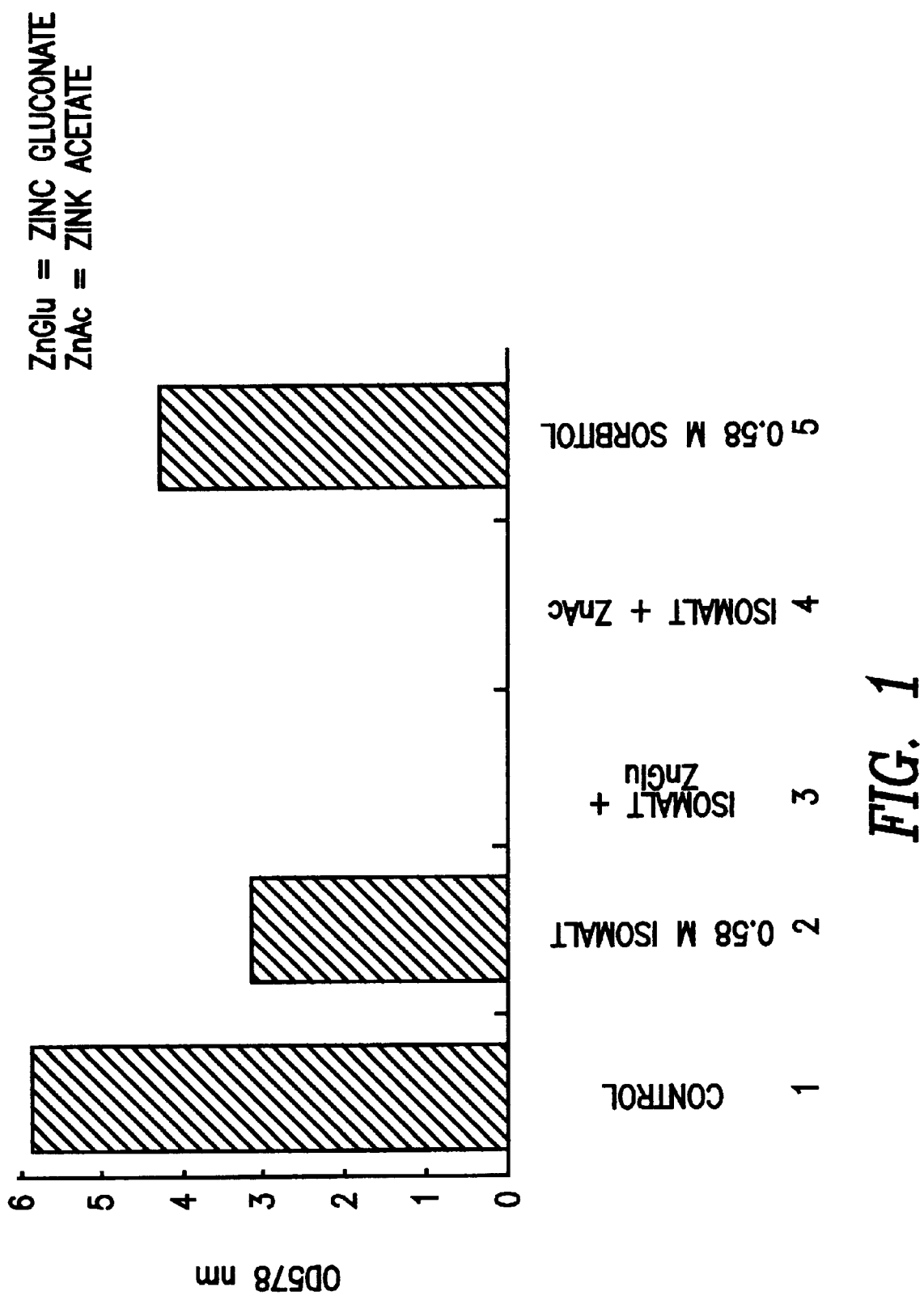
FIG. 1 plots the influence of isomalt and zinc salt and of comparative substances on the growth of Staphylococcus aureus.

Staphylococcus aureus was cultivated at 37° C. in CASO medium to which, in addition to the carbon source glucose (5% strength), isomalt (0.58 M) had been added. The growth of the bacteria cultures in a shaking flask was determined after 16 h by means of the optical density ($OD_{578}$) and compared with a control (CASO medium without isomalt). It was observed that in all experiments the growth of the cultures which were grown in isomalt was inhibited by more than 50%. In comparison, the growth in equimolar amounts of sorbitol (0.58 M) was only reduced to about 75% (see FIG. 1, samples 1, 2 and 5).

Figure 2:
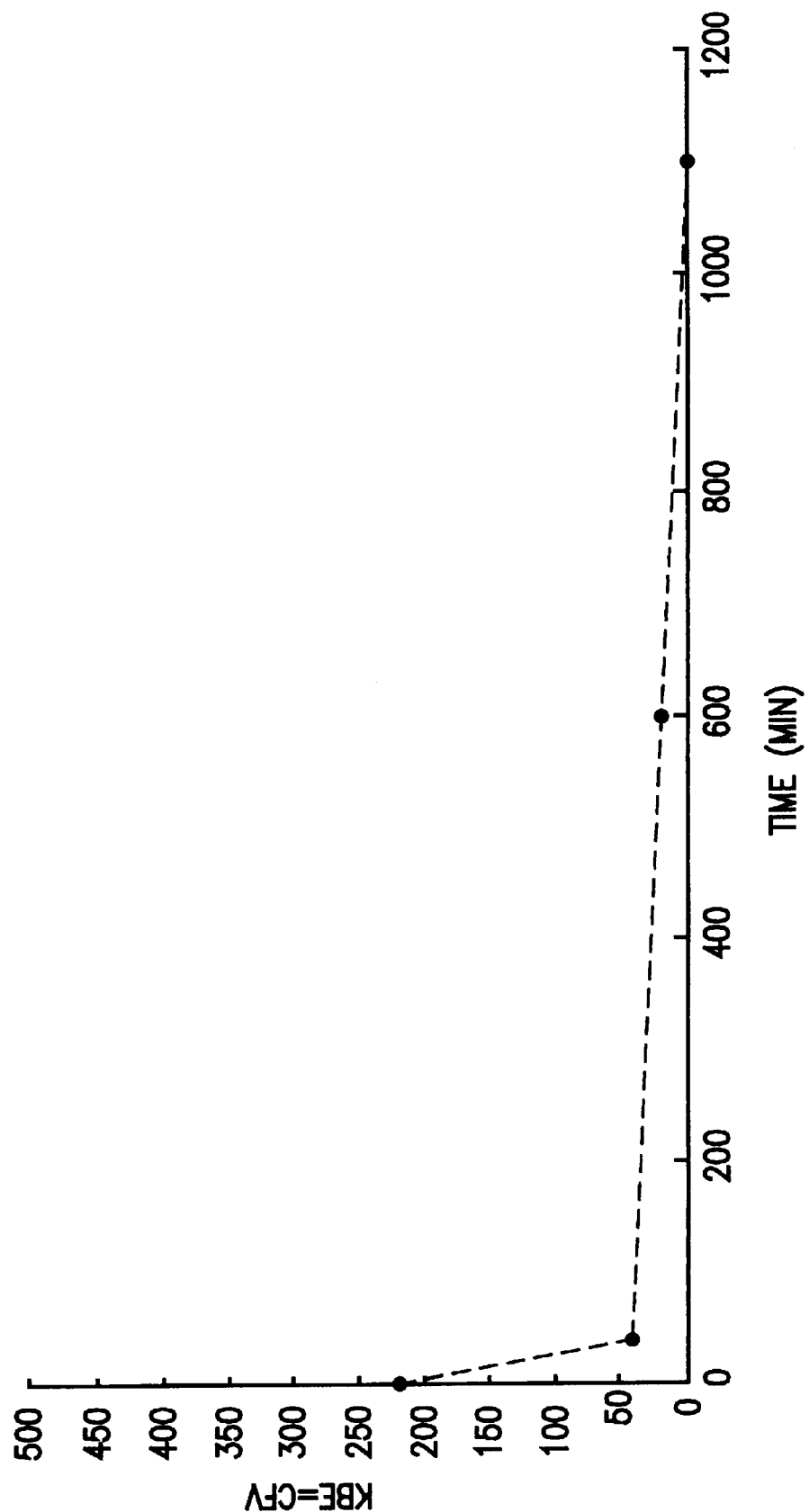
FIG. 2 plots the mortality of Staphylococcus aureus in 60% strength 1,6-GPS-enriched solution (80 parts of 1,6-GPS:20 parts of 1,1-GPM) and FIG. 3 plots the mortality of Streptococcus pneumoniae in 60% strength 1,6-GPS-enriched solution (80 parts of 1,6-GPS and 20 parts of 1,1-GPM).

Furthermore, an antibacterial effect of a 60% strength 1,6-GPS-enriched solution (80/20 parts of 1,6-GPS/1,1-GPM) could be demonstrated (see FIG. 2 for the mortality of Staphylococcus aureus).

The highly concentrated 60% strength 1,6-GPS-enriched solution was contaminated with approximately 1000 germs of various bacteria (Staphylococcus aureus), and samples were taken at various intervals. The germs that survived in the solution were made visible by filtration through a filter (0.45 µm) and incubation of the filter on selective agar substrates. It could be demonstrated that even after 30 min the number of germs was reduced considerably and that after one day (1140 min) bacteria were almost no longer detectable.

Example 2

Antibacterial Effect of Zinc/Isomalt

Hard isomalt candies into which zinc gluconate or zinc acetate (2.5 mg of zinc per g of isomalt) had been incorporated were dissolved in CASO medium to give a 20% strength (w/v) mixture, which was inoculated with a fresh Staphylococcus aureus culture. The growth of the bacteria at 37° C. in a shaking flask was determined after 16 h by means of the optical density ($OD_{578}$) and compared with a control (CASO medium without hard candies). Neither the combination isomalt/zinc gluconate nor isomalt/zinc acetate permitted growth of the bacteria. For all cultures, optical densities of 0.0 were measured (see FIG. 1, samples 3 and 4).

Example 3

Determination of Free Zn Ions in Sugar, Sugar Alcohol and Hard Candy Solutions 10 ml of zinc gluconate solution (2 g of zinc gluconate and 250 ml of deionized water) are mixed with 10 ml of polyol solution (1.0 g of sugar or sugar alcohol dissolved in 25 ml of deionized water) and 2 ml of acetate buffer (pH=6.0) and thermostatted at 35° C. in a cuvette.

1 molar $NaHCO_3$ solution is subsequently added dropwise in small amounts, and the turbidity is determined using a turbidity photometer.

Isomalt, sucrose, glucose, hard isomalt candies, the zinc gluconate which was used as a source of zinc and two commercial products are compared, the overall amount of Zn ions in each case corresponding to 26 mg in 50 ml of solution.

Free zinc ions and their percentage (of the total amount) show that, in the presence of isomalt (even as hard candy), a relatively large number of free zinc ions is present in comparison to other polyols.

TABLE 1

Nephelometric determination of free Zn ions in the presence of polyols

| Sugar/sugar alcohol/ hard candy | Zn ions free in solution* (in mg in 50 ml of solution) | Percentage of free (uncomplexed) ions (in %) |
|---|---|---|
| Isomalt | 15.11 | 58 |
| Glucose | 13.00 | 50 |
| Sucrose | 12.40 | 48 |
| Isomalt/hard candies | 10.40 | 40 |
| Hard candies commercial product A | 3.90 | 15 |
| Hard candies commercial product B | 3.80 | 15 |
| Zn gluconate | 14.62 | 64 |

*Standardized to the same Zn ion concentration (Commercial product A: hard candy made of sucrose syrup/glucose syrup admixed with zinc gluconate; Commercial product B: hard candy made of sucrose syrup/glucose syrup admixed with zinc gluconate and lemon aroma.)

Example 4

Mortality Kinetics of Streptococcus pneumoniae in 60% Strength 1,6-GPS/1,1-GPM Solution (80/20)

1. Contamination With a Low Number of Germs (100 CFU/ml)

Using a freshly grown Streptococcus pneumoniae culture, a 60% strength 1,6-GPS/1,1-GPM (80/20) solution was inoculated with a final number of germs of 100 CFU/ml. Samples of 0.1; 1.0 and 10.0 ml were taken and filtered through membrane filters (pore diameter 0.45 µm), and the filters were incubated on a streptococci substrate in order to visualize surviving germs.

Result: Even in the zero sample, i.e. after a mixing time of 10 min, no surviving germs could be detected.

2. Contamination With a Higher Number of Germs ($4 \times 10^4$ CFU/ml)

The experiment was carried out as described above, but the initial number of germs was set to 40,000 CFU/ml.

Figure 3:
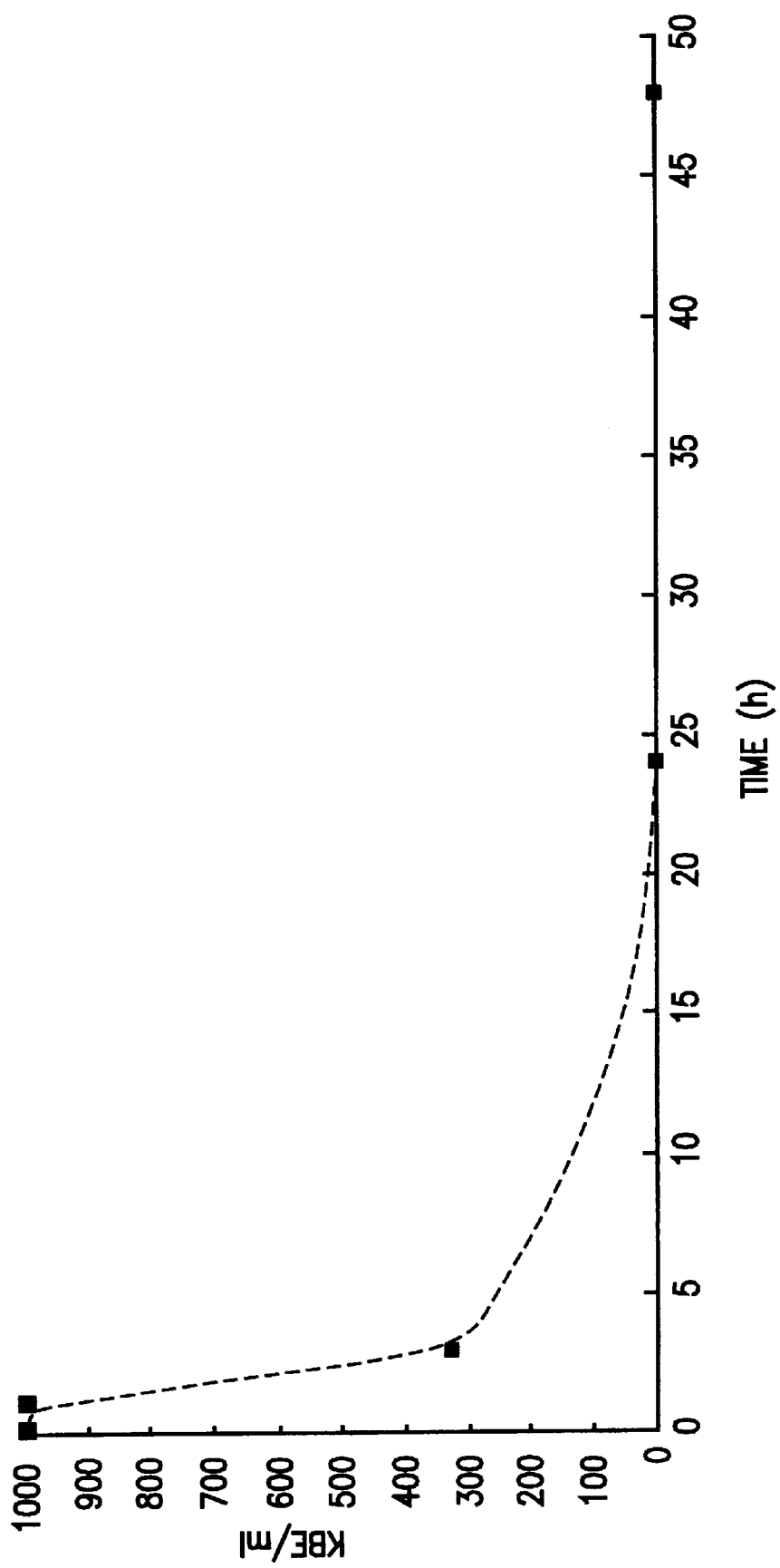

Result: After the mixing time of 10 min, only 1000 germs/ml could still be detected. This number remained unchanged after 1 h (see Table 1 and FIG. 3). However, after 3 h the number of germs decreased significantly, only 330 CFU/ml could still be detected, while both after 24 h and after 48 h, no more streptococci could be isolated from the 60% strength 1,6-GPS/1,1-GPM solution.

TABLE 2

Mortality of *Streptococcus pneumoniae*
in a 60% strength 1,6-GPS/1,1-GPN solution (80/20)

| Time (h) | CFU/ml |
| --- | --- |
| 0 | 1000 |
| 1 | 1000 |
| 3 | 330 |
| 24 | 0 |
| 48 | 0 |

Table 2: The 60% strength solution was inoculated with an initial number of germs of 40,000 CFU/ml; however, after the 0 interval (after approximately 10 min of mixing time), only 1000 CFU/ml could still be detected.

Although the present invention has been described in relation to particular embodiments thereof, many other variations and modifications and other uses will become apparent to those skilled in the art.

What is claimed is:

1. A food or pharmaceutical containing zinc and also an antimicrobially effective amount of a sugar alcohol mixture comprising 1,6-GPS (6-O-α-D-glucopyranosyl-D-sorbitol) and 1,1-GPM (1-O-α-D-glucopyranosyl-D-mannitol).

2. The food or pharmaceutical as claimed in claim 1, wherein 1,6-GPS and 1,1-GPM are present in the sugar alcohol mixture in about equimolar amounts.

3. The food or pharmaceutical as claimed in claim 1, wherein the 1,1-GPM is 1–42 or 58–99 w % of the mixture of 1,6-GPS and 1,1-GPM.

4. The food or pharmaceutical as claimed in claim 3, wherein the sugar alcohol mixture additionally contains 1,1-GPS (1-O-α-D-glucopyranosyl-D-sorbitol).

5. The food or pharmaceutical as claimed in claim 1, wherein the zinc is present as zinc gluconate or zinc acetate.

6. The food or pharmaceutical as claimed in claim 4, wherein the zinc is present in the form of organic or inorganic zinc salts.

7. The food or pharmaceutical as claimed in claim 6, wherein the zinc salt is zinc gluconate or zinc acetate.

8. The food or pharmaceutical as claimed in claim 1, wherein the sugar alcohol mixture additionally contains 1,1-GPS (1-O-α-D-glucopyranosyl-D-sorbitol).

9. The food or pharmaceutical as claimed in claim 8, wherein the zinc is present in the form of organic or inorganic zinc salts.

10. The food or pharmaceutical as claimed in claim 9, wherein the zinc salt is zinc gluconate or zinc acetate.

11. A method of imparting an antimicrobial effect to a food or pharmaceutical which comprises combining said food or pharmaceutical with an antimicrobially effective amount with a sugar alcohol mixture comprising 1,6-GPS (6-O-α-D-glucopyranosyl-D-sorbitol) and 1,1-GPM (1-O-α-D-glucopyranosyl-D-mannitol).

12. The method of claim 11 wherein the 1,6-GPS and 1,1-GPM are present in the sugar alcohol mixture in about equimolar amounts.

13. The method of claim 11 wherein the sugar alcohol mixture additionally contains zinc.

14. A product for consumption by humans or animals, which comprises 1,6-GPS (6-O-α-D-glucopyranosyl-D-sorbitol) and 1,1-GPM (1-O-α-D-glucopyranosyl-D-mannitol) and a pharmacologically effective amount of zinc.

15. The method of claim 13 wherein the zinc is present in the form of zinc gluconate or zinc acetate.

16. The product as claimed in claim 14, wherein the product additionally contains 1,1-GPS.

17. The product as claimed in claim 16, wherein the product contains 1,1-GPM and 1,6-GPS in about equimolar amounts.

18. The product as claimed in claim 17, wherein zinc is present in the form of inorganic or organic zinc salts.

19. The product as claimed in claim 14, wherein the product contains 1,1-GPM and 1,6-GPS in about equimolar amounts.

20. The product as claimed in claim 19, wherein zinc is present in the form of inorganic or organic zinc salts.

* * * * *